United States Patent [19]

Kende et al.

[11] 4,059,593

[45] Nov. 22, 1977

[54] SYNTHESIS OF STEGANACIN AND DERIVATIVES THEREOF

[75] Inventors: Andrew S. Kende, Pittsford; Lanny S. Liebeskind, Snyder, both of N.Y.

[73] Assignee: University of Rochester, Rochester, N.Y.

[21] Appl. No.: 715,487

[22] Filed: Aug. 18, 1976

Related U.S. Application Data

[62] Division of Ser. No. 642,954, Dec. 22, 1975, Pat. No. 4,003,916.

[51] Int. Cl.$^2$ ............................................ C07D 317/44
[52] U.S. Cl. ............................................. 260/340.5 R
[58] Field of Search ...................... 260/340.5, 340.5 R

[56] References Cited

PUBLICATIONS

Becker et al., J. Chem. Soc., Chem. Commun., pp. 430-431 (1974).
Hughes et al., Tetrahedron Letters, No. 18, pp. 1543-1546 (May, 1976).
Kende et al., J. Am. Chem. Soc. 98, pp. 267-268 (1976).

Primary Examiner—Ethel G. Love
Attorney, Agent, or Firm—Richard R. Lloyd

[57] ABSTRACT

Steganacin and Steganangin, dibenzocyclooctadiene lignan lactones, have been reported to possess antileukemic activity. This invention describes the first total synthesis of these compounds and other relevant intermediates.

2 Claims, No Drawings

SYNTHESIS OF STEGANACIN AND DERIVATIVES THEREOF

The invention described herein was made in the course of Grant No. CA-11326 from the National Cancer Institute, Department of Health, Education and Welfare.

CROSS-REFERENCE TO RELATED APPLICATIONS

This application is a divisional of our prior, copending application Ser. No. 642,954, filed Dec. 22, 1975, now U.S. Pat. No. 4,003,916.

BACKGROUND OF THE INVENTION

1. Field of the Invention

This invention relates to a new and novel process for the synthesis of compounds heretofore known only as naturally occurring substances. Specifically, these compounds were heretofore isolated from *Steganotaenia araliacea*, a plant native to Ethiopia, by extraction with alcohol.

2. Description of the Prior Art

A. Steganacin and Steganangin are described as possessing anti-leukemic activity in the article of Kupchan, Britton, Ziegler, Gilmore, Restino and Bryan, Journal of the American Chemical Society, 95 (4), 1335 (1973). The article also describes the compounds known as Steganone and Episteganol.

SUMMARY OF THE INVENTION

A new and novel synthesis of steganacin, which compound has the structure

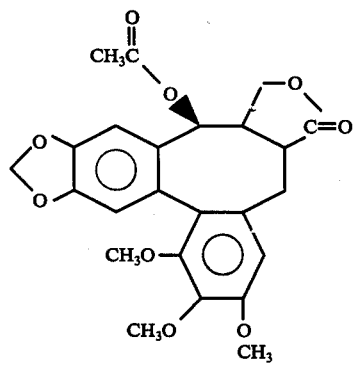

I, has been discovered, which process produces the racemic mixture of compound I in approximately 10% yield. The starting material in the synthetic scheme is homopiperonyl alcohol.

COMPLETE DISCLOSURE

The isolation and structure determination of a novel class of dibenzocyclooctadiene lignan lactones represented by the anti-leukemic esters steganacin (I) and steganangin (II) have been described recently by Kupchan and his collaborators [J. Am. Chem. Soc., 95, 1335 (1973)].

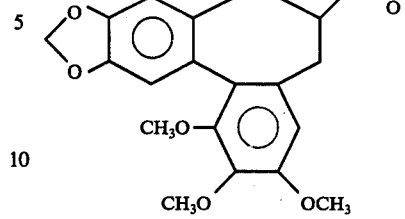

I, R=COCH$_3$

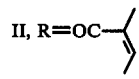

III, R=H

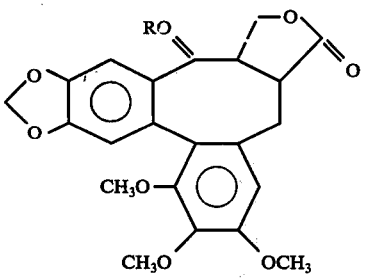

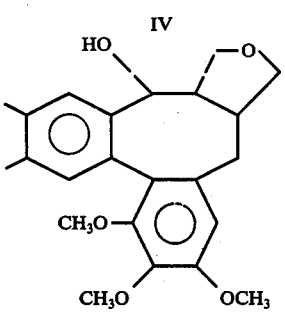

V

In view of the interesting chemical and biological properties of these compounds, it was an object of the present invention to totally synthesize these compounds from readily available starting materials.

The object of the invention has been achieved by the provision of a short and efficient route suitable for large scale preparation of these rare natural lactones known as steganacin (I), steganangin (II), steganol (III), steganone (IV) and episteganol (V). The total synthesis produces these compounds as racemic mixtures.

The synthesis rests upon three strategic principles: (a) utilization of diethyl malonate as a lynch-pin upon which both aromatic residues are elaborated, (b) formation of the eight-membered ring by non-phenolic oxidative coupling and (c) late introduction of functionality at C-5 and subsequent generation of the trans-fused lactone ring at C-6 and C-7. The attempted oxidative closures of C-5 oxygenated precursors (ketone, ketal, alcohol, protected alcohol) did not produce the desired eight-membered ring system.
The ring system of this series of compounds is numbered as follows:
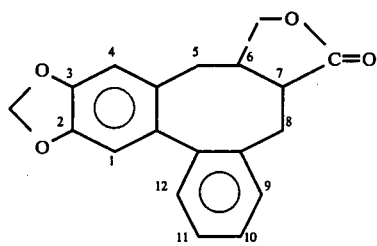
The compounds of the process are prepared as illustrated in Chart I.
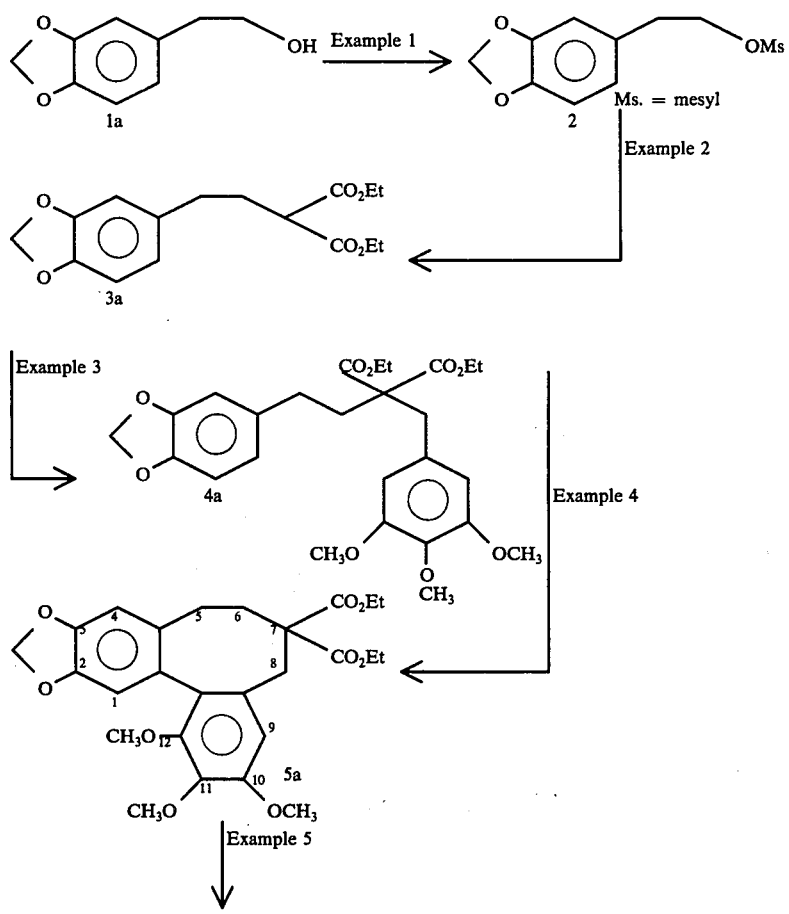

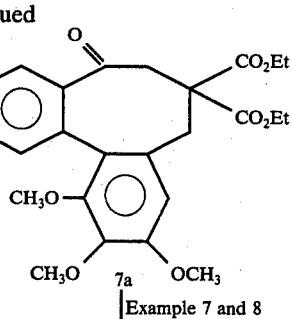
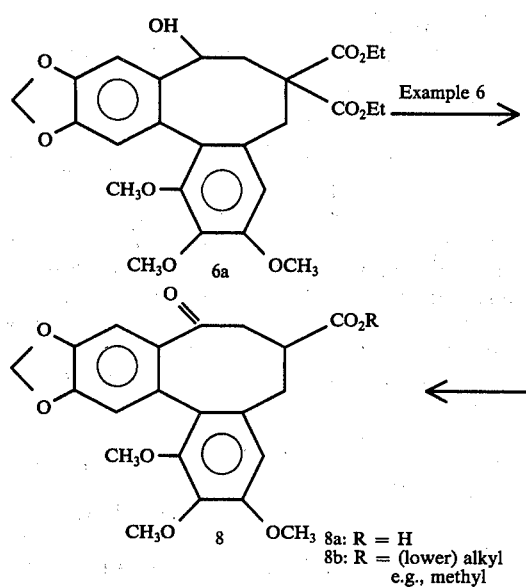
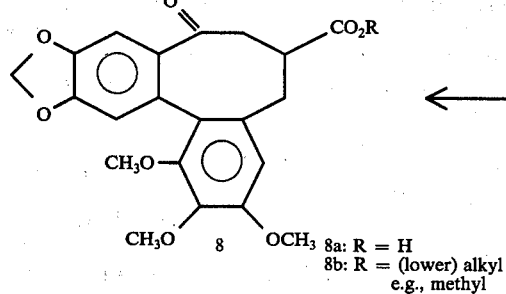

8a: R = H
8b: R = (lower) alkyl
   e.g., methyl

Example 9

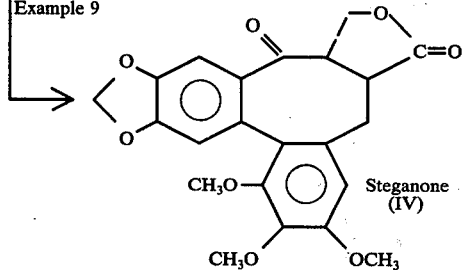

Steganone (IV)

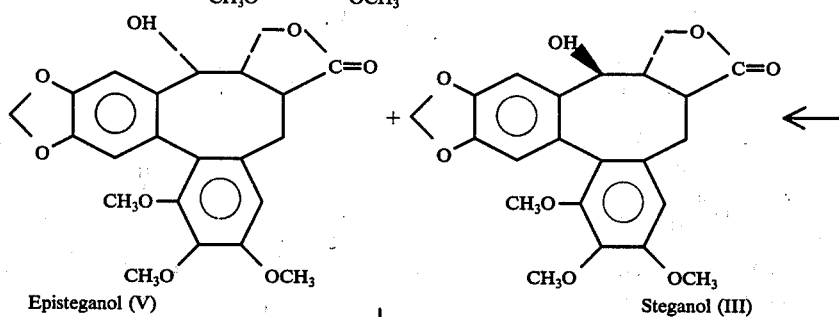

Episteganol (V)    Steganol (III)

Example 11

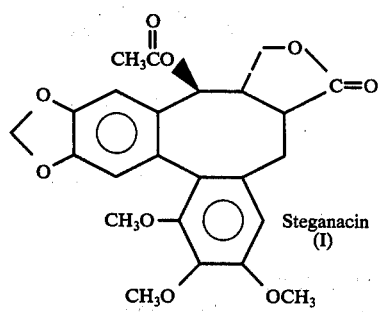

Steganacin (I)

Homopiperonyl alcohol 1, prepared from piperonal in 78% overall yield by modifications of known procedures (R. G. Neak, R. S. Wheeler, J. Chem. Soc., 1780 (1938) was converted (CH₃SO₂Cl/Et₃N, CH₂Cl₂, 0° C., 20 mins.) to the oily mesylate 2 which was treated with 2.2 equivalents of sodiodiethyl malonate (benzene, reflux, 18 hrs.). Workup and removal of excess diethyl malonate in vacuo produced crude diester 3, which was alkylated with 3,4,5-trimethoxybenzyl bromide (NaH, dimethylformamide, 0° C., 30 minutes) to yield the crystalline dialkylation product 4a, m.p. 79.5°–81.0° C. in 52% overall yield from alcohol 1. Dropwise addition of a .02M solution of diester 4a in methylene chloride containing 5% trifluoroacetic anhydride to 3.5 molar equivalents of VOF$_3$ (25°, 1 hr.) followed by bicarbonate workup and florisil filtration gave an oil which on trituration with ether gave 45% of nearly colorless crystals, m.p. 110°-111° C., assigned the dibenzocyclooctadiene structure 5a. This substance exhibited, inter alia; nuclear magnetic resonance spectra [NMR] (100 MHz, CDCl$_3$, δ) 6.68, 6.64, 6.56 (3 singlets, aromatic protons) and 3.88, 3.84, 3.52 (3 singlets, OCH$_3$); U.V. max (EtOH) 389, 253, 210; mass spectrum m/e 486 (M+), 471, 441, 422; Infrared [I.R.—CHCl$_3$] 1725 cm$^{-1}$. In the NMR, the methoxyl signal at distinctly higher field (δ3.52) than the other two is characteristic of similarly substituted biaryls [A. Brossi, J. O'Brien and S. Teitel, Helv. Chim. Acta, 52, 678 (1969)] and is attributed to the anisotropic shielding of protons situated above the plane of the aromatic ring.

To introduce an oxygen function at C-5 of this dibenzocyclooctadiene system the following three-stage operation was performed without purification of intermediates. Treatment of diester 5a with freshly recrystallized N-bromosuccinimide (CCl$_4$, reflux, 2 hrs.) with benzoyl peroxide as initiator yields a single monobromosubstitution product which with silver trifluoroacetate (dimethylsulfoxide, 25° C., 1 hr.) followed by workup with aqueous triethylamine gives the hydroxydiester 6a, IR (CHCl$_3$) 3400, 1725 cm$^{-1}$. Direct oxidation of this alcohol with dipyridine-chromium trioxide in methylene chloride or Jones reagent yields on workup and trituration with ether the colorless crystalline ketodiester 7a, m.p. 127°-129° C. in 60% overall yield from the cyclication product 5a at C-5 rather than C-8 was designed into the synthesis by providing the bulky gem-dicarbethoxy substituents on C-7.

Saponification (2.7M KOH, 50% EtOH, reflux, 6hrs.) and decarboxylation (neat, 200°) converted ketodiester 7a into the ketoacid 8a in 95% yield. Treatment of this ketoacid with 37% aqueous formaldehyde (0.4M KOH, H$_2$O, 25° C., 1 hr.) gave in 77% yield a single crystalline lactone, m.p. 229.5°-232.0° C., identical by mass spectrum (M.S.), Ultra Violet (U.V.), 100 MHz NMR (Table 1) and careful chromatographic comparison by high pressure liquid chromatography (HPLC) and thin layer chromatography (TLC) in 8 solvent systems with an authentic sample of natural steganone (IV).

Further proof of identity of our synthetic ketone was available from its reduction with NaBH$_4$ (CH$_2$Cl$_2$/methanol, 25° C., 2 mins.) to give two major products, (±)-steganol (III), m.p. 155°-158° C. (loss of methanol of crystallization) and (±)-episteganol(V), m.p. 215.5°-217.5° C. in the ratio 55:45, respectively, separable by silica gel chromatography (20% cyclohexane in ether). Finally, acetylation of steganol (Ac$_2$O, pyridine, 50° C., 2 hrs.) gave (±)-steganacin, m.p. 212.5°-214.5° C. IR (CHCl$_3$) 1767, 1729 cm$^{-1}$, identical by UV, NMR, MS and both TLC and HPLC chromatography with natural steganacin.

The complete X-ray single crystal structure of episteganol V reported by Kupchan et al. [J. Am. Chem. Soc., 95, 1335 (1973)] reveals that the plane of one phenyl ring is substantially twisted with respect to the plane of the other, so that the correcct molecular structure is represented as Va, below. Since episteganol has been chemically related under mild conditions to steganone and thus to steganol, steganacin and steganangin, it is clear that all of these natural substances possess the corresponding twisted biaryl framework (Va rather than Vb). Such isomerism, also known as atropisomerism, sometimes leads to the formation of two tricyclic diastereomers during our synthetic sequence, only one of which corresponds to the "natural" configuration. However, in general, the "non-natural" diastereomer (cf. Vb) is thermally convertible to an equilibrium mixture containing the "natural" isomer, so that intermediates of both diastereomeric series may be employed for the total synthesis of our target compounds. This point is discussed in the experimental examples dealing with ketoacids 8a and ketoesters 8b.

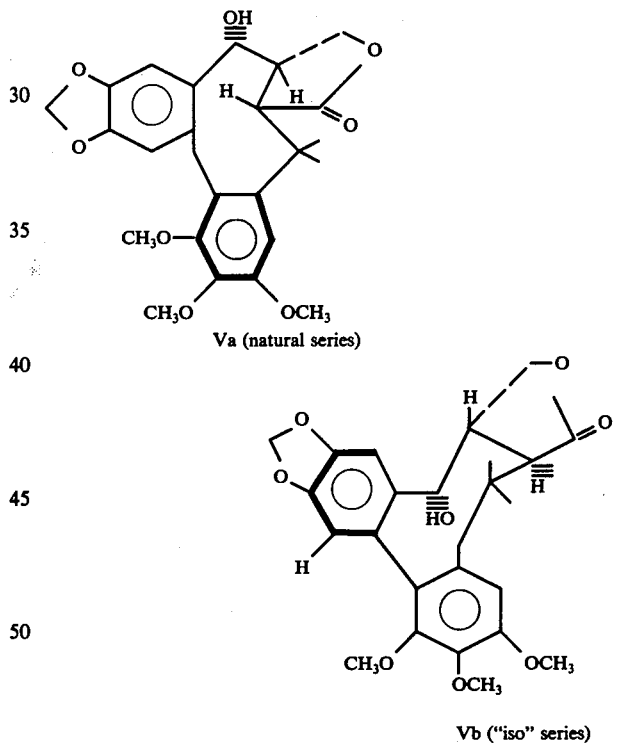

Va (natural series)

Vb ("iso" series)

TABLE II

100 MHz NMR DATA(S) FOR NATURAL AND SYNTHETIC LACTONES

| | | | H4 | H9 | H1 | OCH$_2$O | | H5 | H13 | | OMe | OCOCH$_3$ |
|---|---|---|---|---|---|---|---|---|---|---|---|---|
| IV | Steganone$^a$ | (natural) | 7.53 | 6.63 | 6.53 | 6.10 | | | —4.35 mult$^d$ | 3.89 | 3.60 | |
| IV | Steganone$^{a,c}$ | (synthetic) | 7.53 | 6.63 | 6.53 | 6.10 | | | —4.35 mult | 3.89 | 3.60 | |
| III | Steganol$^b$ | (natural) | 6.78 | 6.57 | 6.45 | 6.02 | | | | 3.91 | 3.87 | 3.73 |
| III | Steganol$^c$ | (synthetic) | 6.78 | 6.57 | 6.45 | 6.02 | br$^d$ | | | 3.89 | 3.85 | 3.73 |
| V | Episteganol$^b$ | (natural) | 7.08 | 6.69 | 6.49 | 6.03 | J=8 | 4.98 J=8$^d$ | | 3.87 | 3.62 | |
| V | Episteganol$^c$ | (synthetic) | 7.08 | 6.69 | 6.50 | 6.03 | J=4 | 4.96 J=8$^d$ | | 3.89 | 3.59 | |
| I | Steganacin$^a$ | (natural) | 6.90 | 6.60 | 6.44 | 6.03 | | 5.82 J=8$^d$ | | 3.91 | 3.86 | 3.73 | 1.90 |

TABLE II-continued

| | | 100 MHz NMR DATA(S) FOR NATURAL AND SYNTHETIC LACTONES | | | | | | | |
|---|---|---|---|---|---|---|---|---|---|
| | | H4 | H9 | H1 | OCH$_2$O | H5 | H13 | OMe | OCOCH$_3$ |
| I | Steganacin[a,c] (synthetic) | 6.90 | 6.60 | 6.44 | 6.02 | 5.81 J=7[d] | | 3.91 3.86 | 3.72 1.89 |

[a]Data recorded on a Jeol PFT 100 MHz NMR instrument. These Fourier PMR δ-values for natural steganone are in agreement with δ-values from our CW 100 MHz measurements (CHCl$_3$ calibration) and are reproducibly .04–.08 ppm higher than those previously reported for this material b.
[b]Kupchan et al, J. Am. Chem. Soc., 95, 1335 (1973).
[c]Data recorded on a Jeol CW 100 MHz NMR.
[d]b. reports H13 at: δ4.29 (1H, q, B of ABX) and δ4.42 (1H, g, A of ABX); however, our spectra for both natural and synthetic steganone indicate absorptions for H13 are best described as a multiplet.

For the purpose of this disclosure, the term (lower)alkyl shall mean a straight or branched chain alkyl moiety containing 1 to 5 carbon atoms. (Lower)-alkoxy means an alkoxy group having 1 to 5 carbon atoms. The term "metallic or amine cationic salt" shall mean those common salts usually prepared of carboxylic acids; i.e., alkaline and alkaline earth metal salts—sodium, potassium, calcium, magnesium, etc., and those salts prepared by the interaction of a carboxylic acid group with a primary, secondary or tertiary amine-triethylamine, pyridine, dicyclohexylamine, aniline, etc.

A preferred embodiment of the present invention is the compound having the formula

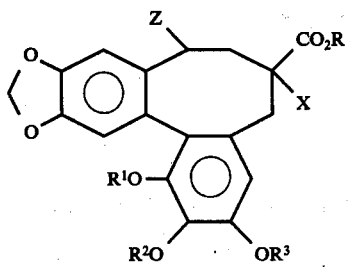

in which Z is H, hydroxy or oxo (=O), X is H or —CO$_2$R, R is H, (lower)alkyl of 1 to 5 carbon atoms, or a radical of the formula

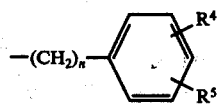

wherein n is an integer of 0 to 5 and R$^4$ and R$^5$ are alike or different and each is H, (lower)alkyl, Cl, Br, I, F, (lower)alkoxy, CF$_3$ or NO$_2$, and R$^1$, R$^2$ and R$^3$ are alike or different and each is H or (lower)alkyl of 1 to 3 carbon atoms; or a metallic or amine cationic salt thereof when R is H.

A preferred embodiment of the present invention is the compound having the formula

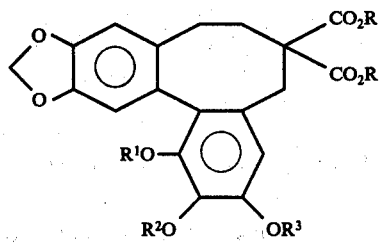

in which R is (lower)alkyl of 1 to 5 carbon atoms, and R$^1$, R$^2$ and R$^3$ are alike or different and each is H or (lower)alkyl of 1 to 3 carbon atoms.

Another preferred embodiment of the present invention is the compound having the formula

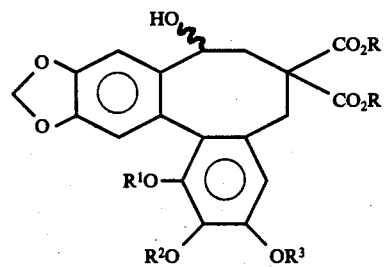

in which R is (lower)alkyl of 1 to 5 carbon atoms, R$^1$, R$^2$ and R$^3$ are alike or different and each is H or (lower)alkyl of 1 to 3 carbon atoms.

Another preferred embodiment is the compound having the formula

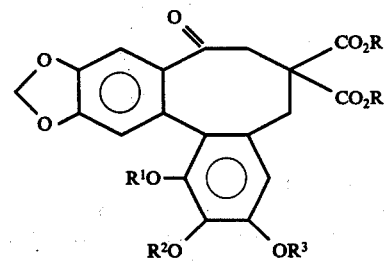

in which R is (lower)alkyl of 1 to 5 carbon atoms, and R$^1$, R$^2$ and R$^3$ are alike or different and each is H or (lower)alkyl of 1 to 3 carbon atoms.

A more preferred embodiment of the present invention is the compound having the formula

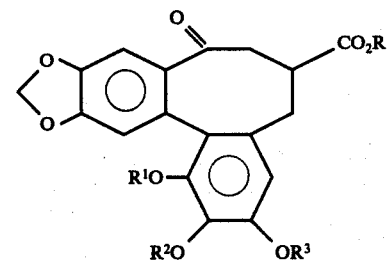

in which R is H, (lower)alkyl of 1 to 5 carbon atoms or a radical having the formula

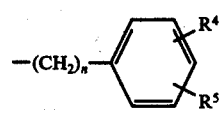

wherein n is an integer of 0 to 5 and R$^4$ and R$^5$ are alike or different and each is H, (lower)alkyl, Cl, Br, I, F, (lower)alkoy, $CF_3$ or $NO_2$, and $R^1$, $R^2$ and $R^3$ are alike or different and each is H or (lower)alkyl of 1 to 3 carbon atoms; or a metallic or amine cationic salt thereof when R is H.

A still more preferred embodiment is the compound having the formula

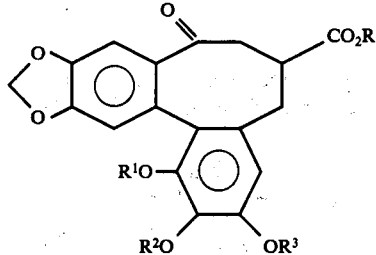

in which R is H or (lower)alkyl of 1 to 5 carbon atoms, and $R^1$, $R^2$ and $R^3$ are alike or different and each is (lower)alkyl of 1 to 2 carbon atoms; or a metallic or amine cationic salt thereof when R is H.

A most preferred embodiment of the present invention is the compound having the formula

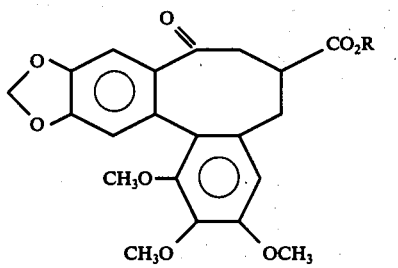

in which R is H or (lower)alkyl of 1 to 5 carbon atoms; or a metallic or amine cationic salt thereof when R is H.

The most preferred embodiment of the present invention is the compound having the formula

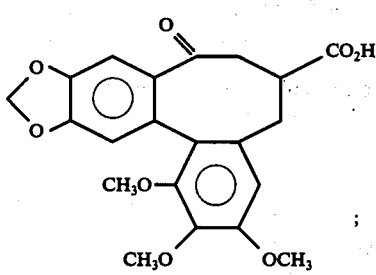

or the sodium or potassium salt thereof.

A preferred embodiment of the present invention is the process for the preparation of the compound having the formula

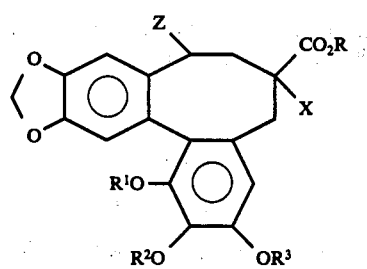

in which Z is H, hydroxy, or oxo (=O), X is H or —$CO_2R$ is H, (lower)alkyl of 1 to 5 carbon atoms or a radical of the formula

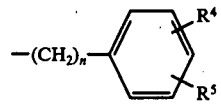

wherein $n$ is an integer of 0 to 5 and $R^4$ and $R^5$ are alike or different and each is H, (lower)alkyl, Cl, Br, I, F, (lower)alkoxy, $CF_3$ or $NO_2$, and $R^1$, $R^2$ and $R^3$ are alike or different and each is H or (lower)-alkyl of 1 to 3 carbon atoms, which process comprises the consecutive steps of A. treating the compound having the formula

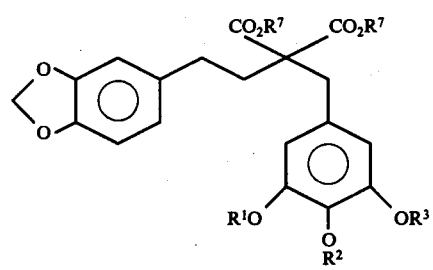

in which $R^1$ is (lower)alkyl of 1 to 5 carbon atoms or a radical having the formula

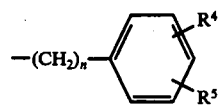

wherein $n$ is an integer of 0 to 5 and $R^4$ and $R^5$ are alike or different and each is H, Cl, Br, I, (lower)-alkoxy, $CF_3$ or $NO_2$, with an excess of $VOF_3$ or $VOCl_3$ in the presence of trifluoroacetic anhydride to produce the compound having the formula

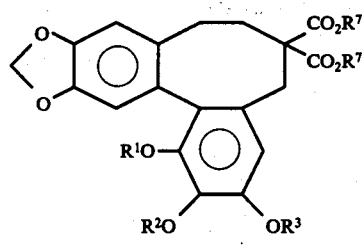

in which $R^7$, $R^1$, $R^2$ and $R^3$ are as defined above; and when desired

B. heating compound 5 with N-bromosuccinimide in the presence of a catalytic amount of benzoyl peroxide, followed by silver trifluoroacetate, then a mild base to produce the compound having the formula

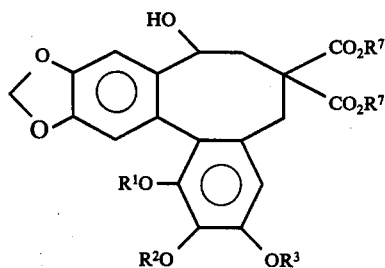

in which R⁷, R¹, R² and R³ are as defined above; and when desired

C. treating compound 6 with an oxidizing agent to produce the compound having the formula

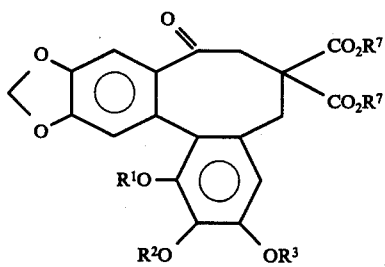

in which R⁷, R¹, R² and R³ are as defined above; and when desired

D. saponifying compound 7 to produce the corresponding ketodiacid, then heating this ketodiacid until decarboxylation occurs to produce the compound having the formula

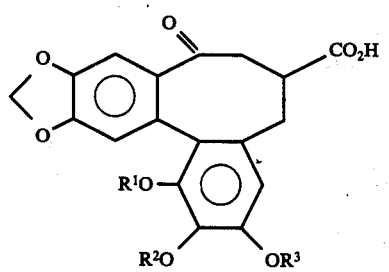

in which R¹, R² and R³ are as defined above; and when desired

E. esterifying compound 8a to produce the compound having the formula

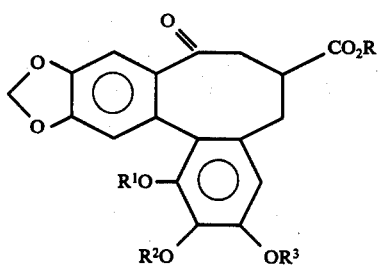

in which R is (lower)alkyl of 1 to 5 carbon atoms or a radical having the formula

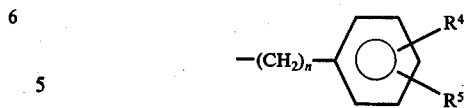

wherein $n$ is an integer of 0 to 5 and $R^4$ and $R^5$ are alike or different and each is H, (lower)-alkyl, Cl, Br, I, F, (lower)alkoxy, $CF_3$ or $NO_2$.

Another preferred embodiment of the present invention is the process for the preparation of the compound having the formula

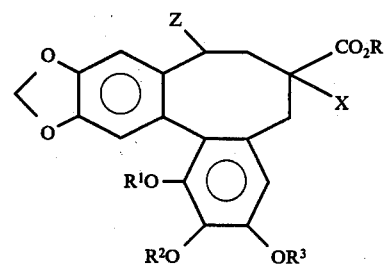

in which Z is H, hydroxy or oxo (=O), X is H or —$CO_2R$, R is H, (lower)alkyl of 1 to 5 carbon atoms or a radical of the formula

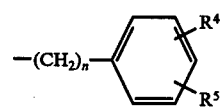

wherein $n$ is an integer of 0 to 5 and $R^4$ and $R^5$ are alike or different and each is H, (lower)alkyl, Cl, Br, I, F, (lower)alkoxy, $CF_3$ or $NO_2$ and $R^1$, $R^2$ and $R^3$ are alike or different and each is H or (lower)alkyl of 1 to 3 carbon atoms, which process comprises the consecutive steps of A. treating the compound having the formula

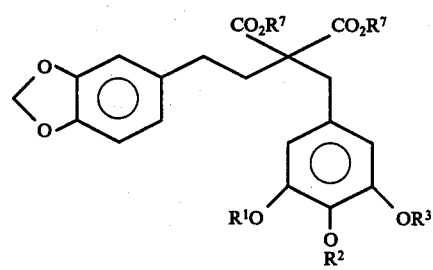

in which $R^7$ is (lower)alkyl of 1 to 5 carbon atoms or a radical having the formula

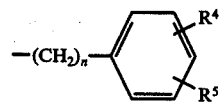

wherein $n$ is an integer of 0 to 5 and $R^4$ and $R^5$ are alike or different and each is H, Cl, Br, I, (lower)alkyl, F, (lower)alkoxy, $CF_3$ or $NO_2$, with an excess of $VOF_3$ or $VOCl_3$ in methylene chloride containing 5% trifluoroacetic anhydride to produce the compound having the formula

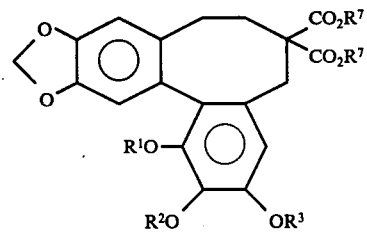

in which $R^7$, $R^1$, $R^2$ and $R^3$ are as defined above; and when desired

B. heating compound 5 with excess N-bromosuccinimide in the presence of a catalytic amount of benzoyl peroxide in a reaction inert solvent, then after removing the solvent, treating the result intermediate with excess silver trifluoroacetate in dimethylsulfoxide, and treating the resultant ester with a mild base to produce the compound having the formula

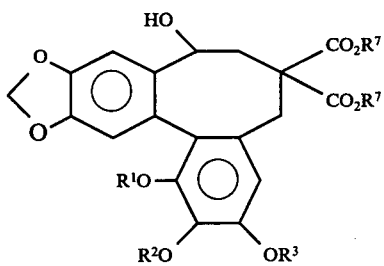

in which $R^7$, $R^1$, $R^2$ and $R^3$ are as defined above; and when desired

C. treating compound 6 with dipyridine-chromium trixodie or Jones reagent ($CrO_3$-aq. acetone-$H_2SO_4$) in a reaction inert solvent to produce the compound having the formula

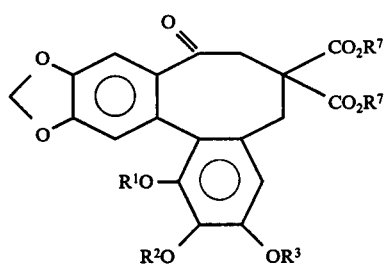

in which $R^7$, $R^1$, $R^2$ and $R^3$ are as defined above; and when desired

D. saponifying compound 7 with about 1.3 M KOH in aqueous ethanol to produce the corresponding ketodiacid potassium salt, then acidifying the solution, isolating the ketodiacid and heating the ketodiacid neat to about 200° C. until decarboxylation occurs to produce the compound having the formula

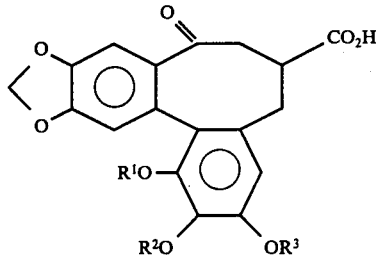

in which $R^1$, $R^2$ and $R^3$ are as defined above; and when desired

E. esterifying compound 8a to produce the compound having the formula

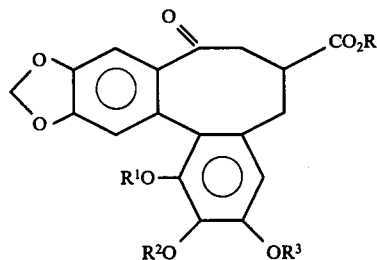

in which R is (lower)alkyl of 1 to 5 carbon atoms or a radical having the formula

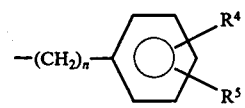

wherein $n$ is an integer of 0 to 5 and $R^4$ and $R^5$ are alike or different and each is H, (lower)alkyl, Cl, Br, I, F, (lower)alkoxy, $CF_3$ or $NO_2$ and $R^1$, $R^2$ and $R^3$ are alike or different and each is H or (lower)alkyl of 1 to 3 carbon atoms.

Another preferred embodiment of the present invention is the process for the preparation of the compound having the formula

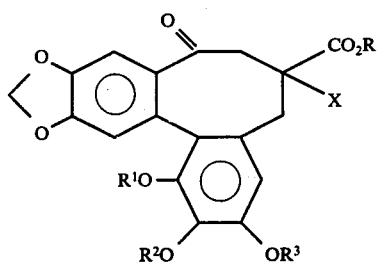

in which X is H or —$CO_2R$, R is H, (lower)alkyl of 1 to 5 carbon atoms or a radical of the formula

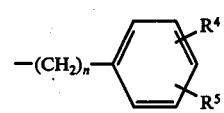

wherein $n$ is an integer of 0 to 5 and $R^4$ and $R^5$ are alike or different and each is H, (lower)alkyl, Cl, Br, I, F, (lower)alkoxy, $CF_3$ or $NO_2$ and $R^1$, $R^2$ and $R^3$ are alike or different and each is H or (lower)alkyl of 1 to 3 carbon atoms, which process comprises the consecutive steps of A. treating the compound having the formula

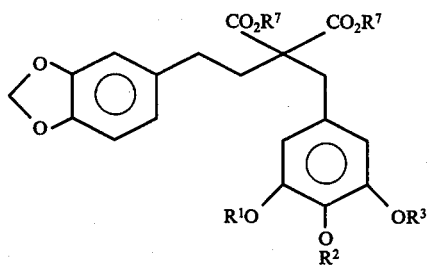

in which $R^7$ is (lower)alkyl of 1 to 5 carbon atoms or a radical having the formula

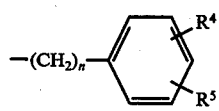

wherein $n$ is an integer of 0 to 5 and $R^4$ and $R^5$ are alike or different and each is H, Cl, Br, I, (lower)alkyl, F, (lower)alkoxy, $CF_3$ or $NO_2$, with an excess of $VOF_3$ in methylene chloride containing 5% trifluoroacetic anhydride to produce the compound having the formula

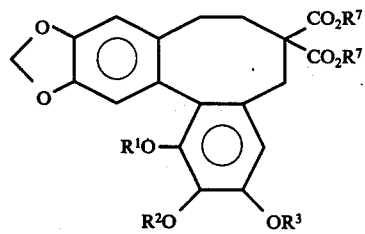

in which $R^7$, $R^1$, $R^2$ and $R^3$ are as defined above;

B. heating compound 5 with excess N-bromosuccinimide in the presence of a catalytic amount of benzoyl peroxide in a reaction inert solvent, then after removing the solvent, treating the resultant intermediate with excess silver trifluoroacetate in dimethylsulfoxide, then treating the resultant trifluoroacetate ester with a mild base to produce the compound having the formula

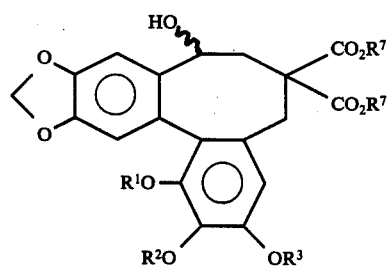

in which $R^7$, $R^1$, $R^2$ and $R^3$ are as defined above;

C. treating compound 6 with dipyridine-chromium trioxide in a reaction inert solvent to produce the compound having the formula

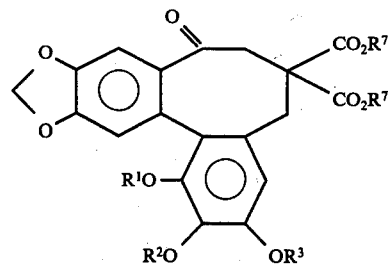

in which $R^7$, $R^1$, $R^2$ and $R^3$ are as defined above; and when desired

D. saponifying compound 7 with about 1.3 M KOH in aqueous ethanol to produce the corresponding ketodiacid potassium salt, then acidifying the solution, isolating the ketodiacid and heating the ketodiacid neat to about 200° C. until decarboxylation occurs to produce the compound having the formula

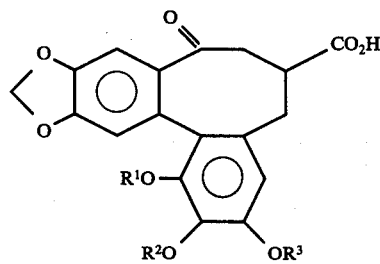

in which $R^1$, $R^2$ and $R^3$ are as defined above; and when desired

E. esterifying compound 8a to produce the compound having the formula

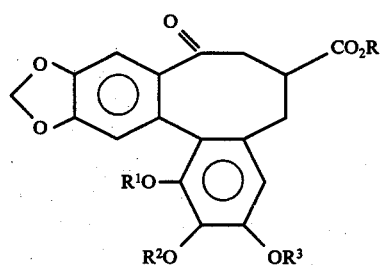

in which R is (lower)alkyl of 1 to 5 carbon atoms or a radical having the formula

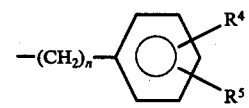

wherein $n$ is an integer of 0 to 5 and $R^4$ and $R^5$ are alike or different and each is H, 8lower)alkyl, Cl, Br, I, F, (lower)alkoxy, $CF_3$ or $NO_2$ and $R^1$, $R^2$ and $R^3$ are alike or different and each is H or (lower)alkyl of 1 to 3 carbon atoms.

A most preferred embodiment of the present invention is the process for the preparation of the compound having the formula

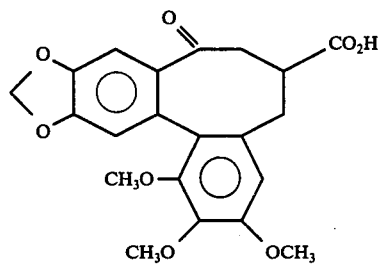

which process comprises the consecutive steps of

A. treating the compound having the formula

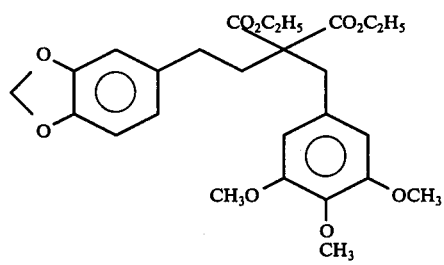

with about four molar equivalents of VOF₃ or VOCl₃ in methylene chloride containing 5% trifluoroacetic anhydride to produce the compound having the formula

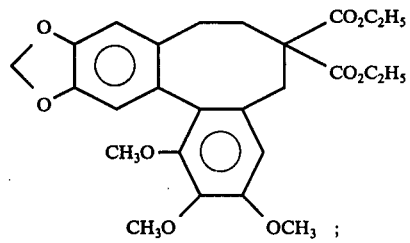

B. heating compound 5a with a 0.5 molar excess of N-bromosuccinimide in the presence of a catalytic amount of benzoyl peroxide in carbon tetrachloride, then after removing the solvent treating the resultant intermediate with a 1.0 molar excess of silver trifluoroacetate in dimethylsulfoxide followed by weak base to produce the compound having the formula

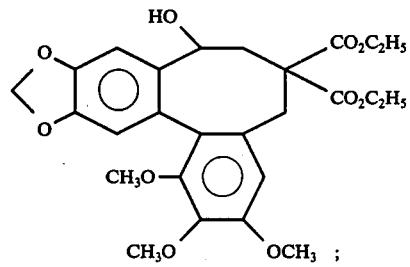

C. treating compound 6a with dipyridine-chromium trioxide in methylene chloride or chromium trioxide in acetone containing aqueous sulfuric acid to produce the compound having the formula

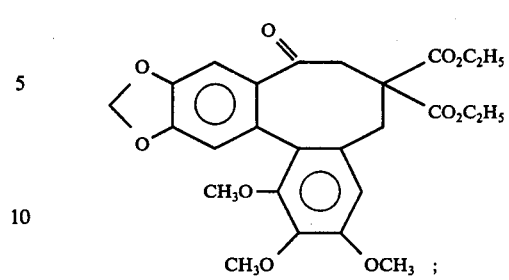

D. saponifying compound 7a with about 1.3 M KOH in aqueous ethanol to produce the corresponding ketodiacid dipotassium salt, then acidifying the solution, isolating the ketodiacid and heating the ketodiacid neat to about 200° C. until decarboxylation occurs to produce the compound having the formula

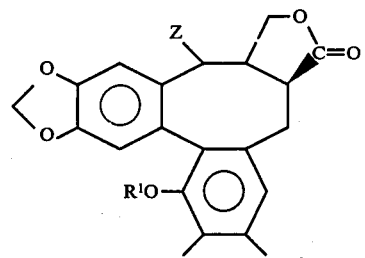

Another preferred embodiment is the process for the preparation of a racemic mixture of the compound having the formula

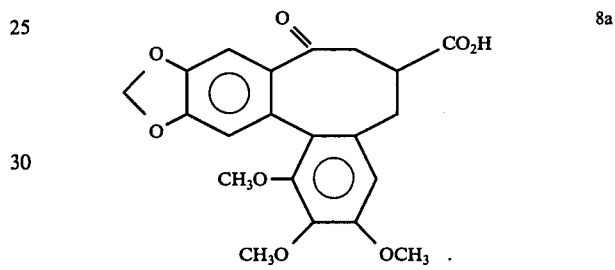

in which Z is ◄OH, oxo (=O) or ◄OW wherein W is acetyl or

and R¹, R² and R³ are alike or different and each is H or (lower)alkyl of 1 to 3 carbon atoms, which process comprises the consecutive steps of A. treating the compound having the formula

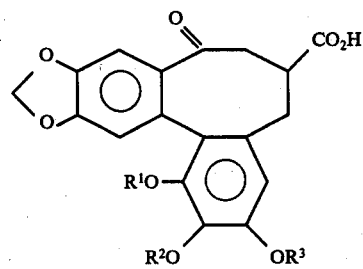

in which R¹, R² and R³ are as defined above, with excess 37% aqueous formaldehyde in the presence of 0.1 to 2M alkali metal hydroxide for 1-48 hours, followed by heating in the presence of excess dilute sulfuric acid and chloroform to produce the compound having the formula

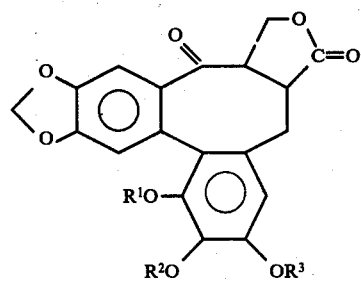
IV in which R¹, R² and R³ are as defined above; and when desired

B. treating compound IV with sodium borohydride in methylene chloride-anhydrous methanol to produce a mixture of the compounds having the formula

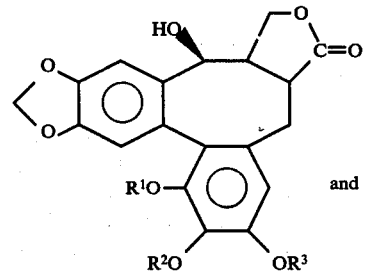
III
and

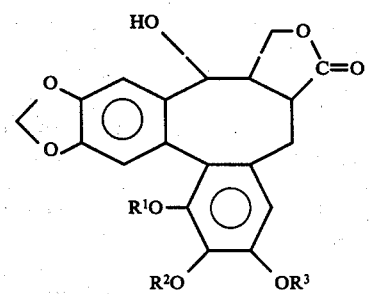
V in which R¹, R² and R³ are as defined above, which mixture is separated into its component parts; and when desired C. acylating compound III with acetic anhydride or angelic acid halide to produce the compound having the formula

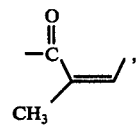

in which W is acetyl or

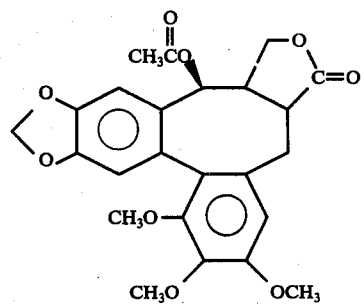

R¹, R² and R³ are as defined above and halide is Cl, Br or I.

A more preferred embodiment is the process for the preparation of a racemic mixture of the compound having the formula

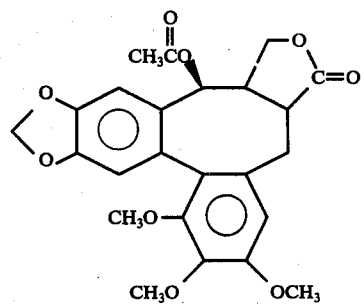
I which process comprises the consecutive steps of

A. treating the compound having the formula

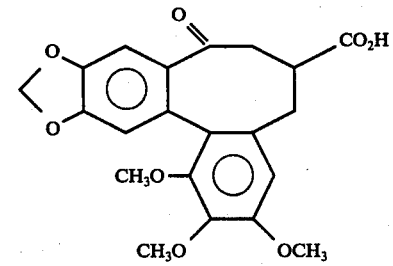

with a 25% molar excess of 37% aqueous formaldehyde in the presence of excess 1N sodium hydroxide at about room temperature for about 40 hours, followed by heating in the presence of excess 10% sulfuric acid and chloroform to produce the compound having the formula

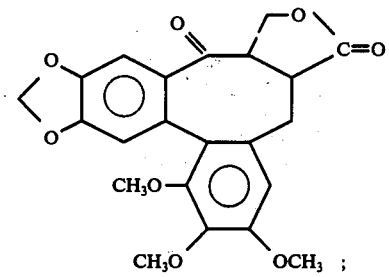

IV

B. treating compound IV with a slight molar excess of sodium borohydride in methylene chloride-anhydrous methanol for about 1 to 5 minutes, followed by quenching in water, to produce a mixture of the compounds having the formula

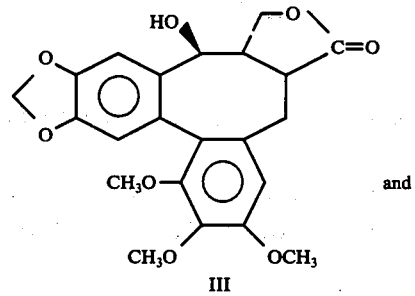

III and

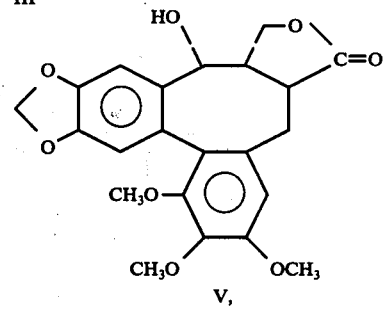

V, which mixture is separated into its components parts; and

C. acylating compound III with acetic anhydride in the presence of a tertiary amine selected from the group consisting of pyridine, trimethylamine, triethylamine, dimethylaniline and n-methylpiperidine with the aid of heat to produce compound I.

EXPERIMENTAL

For the purpose of this disclosure, all melting points cited herein are in degrees Centigrade unless stipulated otherwise.

EXAMPLE 1

2-(3,4-methylenedioxyphenyl)ethyl methane (2)

Homopiperonyl alcohol (1) (7.03g, 42.4 mmol)[1,2,3] and triethylamine (8.59 g., 85.0 mmol) were dissolved in methylene chloride (100 ml). The mixture was cooled to 0°–5°, then methanesulfonyl chloride (7.31 g., 63.6 mmol) was added slowly dropwise to the vigorously stirred solution. The mixture was stirred an additional 30 mins., then transferred to a separatory funnel where it was washed with water (3 × 50 ml), 4% hydrochloric acid (3 × 50 ml), saturated sodium bicarbonate solution (25 ml), saturated brine (25 ml) and dried over sodium sulfate. Filtration and evaporation of the methylene chloride yielded 9.76 g of a brown oil (94%); NMR—(CDCl$_3$) 6.72 (m, 3H), 5.92 (S, 2H), 4.34 (t, J=7, 2H), 2.95 (t, J=7), lying under 2.89 (s) giving a total integration of 5H. This material was used without further purification.

1. M. F. Semmelhack et al., J. Am. Chem. Soc., 94, 8629 (1972).
2. R. G. Niak, R. S. Wheeler, J. Chem. Soc. 1780 (1938). Modifications: (a) NaBH$_4$ reduction of piperonal, (b) HBr gas on a chloroform solution of piperonyl alcohol, (c) phase-transfer catalyzed reaction of the resulting benzyl bromide with NaCN[3], (d) hydrolysis (6M NaOH, 40% EtOH, reflux, 18 hrs.) of the nitrile and (e) LiAlH$_4$ reduction of the resulting 3,4-methylenedioxyphenylacetic acid.
3. C. M. Starks, J. Amer. Chem. Soc., 93, 195 (1971).

EXAMPLE 2

2-Carbethoxy-4-(3,4-methylenedioxyphenyl) butyric acid ethyl ester (3a)

Sodium hydride—50% oil dispersion (1.92 g., 40.0 mmol) was added to a flamed 250 ml round bottom flask. The sodium hydride was washed with hexane, then dry benzene (50 ml) was added. The round bottom flask was equipped with a reflux condenser and an additional funnel which had been charged with diethyl malonate (7.05 g., 44.0 mmol). The apparatus was placed under a nitrogen atmosphere, then the diethyl malonate was added slowly dropwise. The resulting mixture was heated to just below reflux and then crude 2 (4.90 g., 20.0 mmol) in benzene (30 ml) was added all at once to the magnetically stirred solution. The mixture was refluxed 14 hrs. After cooling, it was transferred to a separatory funnel and washed well with water, once with saturated brine (25 ml) and dried over magnesium sulfate. After filtration and the removal of the solvents, the excess diethylmalonate was removed at 1 mm Hg. This produced 5.80 g. of 3 as a pale yellow oil (94%); IR (CHCl$_3$) 1728 cm$^{-1}$; NMR (CDCL$_3$) S 6.64 (M, 3H), 5.89 (S, 2H), 4.09 (g, J=7, 4H), 3.31 (t J=6, 1H), 2.59 (m, 2H), 2.09 (M, 2H), 1.28 (t, J=7, 6H). This material was used as in example 3; however, it can be distilled at 1 mm Hg., 163°–171°.

EXAMPLE 3

2-carbethoxy-2-(3,4,5-trimethoxybenzyl)-4-(3,4-methylenedioxyphenyl)butyric acid ethyl ester (4a)

Sodium hydride—50% oil dispersion (9.6 g., 200 mmol) was added to a flamed 500 ml round-bottom flask and was washed with n-hexane. Dimethylformamide (10 ml) was added and the flask, protected from moisture with a calcium sulfate drying tube, was cooled to 0°–5°. Compound b 3a (30.8 g., 100 mmol) in dimethylformamide (100 ml) was added slowly dropwise with stirring. After the addition was complete, 3,4,5-trimethoxybenzyl bromide[5,6] (27.4 g., 105 mmol) dissolved in dimethylformamide (100 ml) was added slowly dropwise to the stirred mixture maintained near 0°. The reaction was stirred an additional 30 mins. after addition of the benzyl bromide, then absolute ethanol (10 ml) was cautiously added to destroy excess sodium hydride. The reaction mixture was transferred to a separatory funnel and diluted with water (400 ml), and the product was extracted into diethyl ether (4 × 200 ml). The ether layer was washed with water (5 × 100 ml), then saturated brine (100 ml) was dried over sodium sulfate. Filtration and removal of the diethyl ether produced a yellow oil which crystallized on standing. Trituration of the solid with a minimum amount of ether and filtration gave 37 g. of white crystals of 4a (75%)[7], m.p. 79.5°–81.0° C.; IR (CHCl$_3$) 1728 cm$^{-1}$; NMR (CDCl$_3$) s 6.61 (n, 3H), 6.32 (brs, 2H), 5.87 (s, 2H), 4.17 (g, J=7, 4H), 3.80, 3.79 (both S, 9H), 3.25 (br s, 2H), 2.75→1.78 (m, 4H), 1.27 (t, J=7, 6H).

Anal. Calc'd. for $C_{26}H_{37}O_9$: C, 63.96; H, 6.56. Found: C, 63.98; H, 6.59

5. Chem. Abstracts, 70, 96652h (1969).
6. Prepared in >95% yield by NaBH$_4$ reduction of 3,4,5-trimethoxybenzaldehyde followed by bubbling HBr gas through a chloroform solution of the resulting alcohol.
7. All the new compounds prepared in this process gave satisfactory mass spectra, analytical, and spectroscopic data.

EXAMPLE 4

5,6,7,8-tetrahydro-7,7-dicarbethoxy-2,3-methylenedioxy-10,11,12-trimethoxydibenzo[9,c]cyclooctadiene (5a).

VOF$_3$ (3.64g, 21.0 mmol)[8] was transferred with minimum exposure to air to a flamed 500 ml round bottom flask. Methylene chloride containing 5% trifluoroacetic anhydride (30 ml) was added and the flask was fitted with an addition funnel which had been charged with a solution of 4a (2.92 g, 6.0 mmol) in methylene chloride (300 ml) containing 5% trifluoroacetic anhydride. The apparatus was placed under a nitrogen atmosphere and the solution of 4a was added dropwise with vigorous stirring. The reaction mixture was stirred an additional 45 mins. After the addition was completed, it was poured into ice-water (300 ml) containing excess sodium bicarbonate. After the mixture reached room temperature, the organic layer was separated and washed with water (100 ml), then saturated brine (100 ml), and then it was dried over sodium sulfate. Filtration and removal of the solvent leaves a thick oil which was passed through a 12 × 1.5 inch Florisil column with diethyl ether. Removal of the ether and trituration of the residue with methanol yielded 1.25 g. of a yellow solid (43%) which, when recrystallized from methanol, yields white crystals of 5a, m.p. 110°-111° C.; mass spectrum m/e 486; UV (EtOH) 290, 255, 210; IR (CHCl$_3$) 1728 cm$^{-1}$; NMR (CDCl$_3$) δ6.66 (s, 1H), 6.64 (s, 1H), 6.54 (S, 1H) 5.92 (br s, 2H) ~4.10 (overlapping quartets 4H), 3.89 (s, 3H), 3.83 (s, 3H), 3.52 (s, 3H)[9], 3.5→1.5 various absorptions, 1.27 (overlapping triplets, 6H).

Anal. Calc'd. for $C_{26}H_{30}O_9$: C, 64.23; H, 6.17. Found: C, 64.01; H, 6.41.

The crude material after methanol trituration was sufficiently pure to be carried on to the next step.

8. S. M. Kupchan, A. J. Liepa, V. Kameswaran, R. F. Bryan, J. Amer. Chem. Soc., 95, 6861 (1973).
9. A. Brossi, J. O'Brien, S. Teitel, Helv. Chim. Acta, 52, 678 (1969).

EXAMPLE 5

5,6,7,8-tetrahydro-7,7-dicarbethoxy-5-hydroxy-2,3-methylenedioxy-10,11,12-trimethoxy-dibenzo[a,c]-cyclooctadiene (6a)

Compound 5a (4.86 g., 10.0 mmol), N-bromosuccinimide (2.68 g., 15.0 mmol), benzoyl peroxide (0.12 g, 0.5 mmol) and carbon tetrachloride (250 ml) were placed under a nitrogen atmosphere and brought to reflux for 2 hrs.[10] The reaction mixture was cooled and the precipitated succinimide was filtered off. Removal of the carbon tetrachloride yielded an orange oil which was dissolved in dimethylsulfoxide (50 ml). Silver trifluoroacetate (4.41 g., 20.0 mmol) was added all at once and the mixture was stirred for 20 mins. after which time water (5ml) was added, followed by triethylamine (5ml). Stirring was continued for 5 mins. Then the reaction mixture was transferred to a separatory funnel and it was diluted with water (200 ml). The product was extracted into diethyl ether (4 × 100 ml) and the ether layer was then washed with water (3 × 100 ml), 10% sulfuric acid (3 × 100 ml), saturated sodium bicarbonate solution (50 ml), saturated brine (50 ml) and then it was dried over sodium sulfate. Filtration and removal of the solvent yielded an orange oil which rapidly crystallizes. Trituration with a minimum amount of diethyl ether produced 2.1 g of the tan alcohol to 6a (62%): m.p. 151°-154° C; IR (CHCl$_3$) cm$^{-1}$ 3400, 1728; NMR (CDCl$_3$), s 6.69 (s, 1H), 6.56 (s, 1H), 6.41 (s, 1H), 5.98 (br s, 2H), 4.78 (m, 1H), 4.20 (m, 4H), 3.92 (s, 3H), 3.83 (s, 3H), 3.68 (s, 3H), 3.6→1.6 various absorptions, 1.24 (m, 6H).

10. The monobromo compound shows NMR (100 MHz, CDCl$_3$) 5.15δ doublet of doublets, J=11 Hz, J<1 Hz, indicative of benzylic bromination at C-5; IR (CHCl$_3$) 1725 cm$^{-1}$; mass spectrum m/e 565 (M+).

EXAMPLE 6

5,6,7,8-tetrahydro-7,7-dicarbethxoy-2,3-methylenedioxy-10,11,12-trimethoxy-5-oxo-dibenzo[a,c]cyclooctadiene (7a)

Compound 6a (2.1 g, 4.19 mmol) was dissolved in acetone (60 ml) and Jones reagent[11,12] (2.7M, 2 ml, 5.4 mmol) was added dropwise. The reaction is stirred an additional 15 mins., then most of the acetone is removed in vacuo. The resulting residue was partitioned between diethyl ether and water and the ether layer was washed well with water, once with saturated bicarbonate solution, once with saturated brine, and then it was dried over sodium sulfate. Filtration and removal of the ether yielded a solid which when triturated with a small amount of ether gave 1.77 g of 7a (71%); m.p. 127°-129° C; IR (CHCl$_3$) cm$^{-1}$ 1725, 1660; NMR (CDCl$_3$) s 7.48 (s, 1H), 6.58 (s, 1H), 6.45 (s, 1H), 6.01 (br s, 2H), 4.18 (two overlapping quartets, 4H), 3.90 (s, 3H), 3.83 (s, 3H), 3.54 (s, 3H), 3.21 (br s, 2H), 2.88 (AB quartet, 2H), 1.27 (two overlapping triplets, 6H).

Anal. Calc'd. for $C_{26}H_{28}O_{10}$: C, 62.43; H, 5.60. Found: C, 62.00, H, 5.93.

11. Bowers et al., J. Chem. Soc., 2255 (1953).
12. The same oxidation can be carried out usms dipyridine-chromium trioxide, R. Ratcliffe and R. Rodehorst, J. Org. Chem., 35, 4000 (1970).

EXAMPLE 7

5,6,7,8-tetrahydro-7-carboxy-2,3-methylenedioxy-10,11,12-trimethoxy-5-oxo-dibenzo[a,c]cyclooctadiene (8a)

Compound 7a (1.5 g., 3.0 mmol), 95% ethanol (20 ml) and 2.7MKOH (20 ml) were brought under a nitrogen atmosphere and refluxed 6 hrs. The reaction was cooled, transferred to a separatory funnel, diluted with water (100 ml) and all neutral products were washed out with diethyl ether. Acidification with excess 10% sulfuric acid precipitated the diacid which was extracted into diethyl ether (3 × 100 ml). The ether layer was washed with water (50 ml), saturated brine (50 ml) and dried over sodium sulfate. Filtration and evaporation of the ether yielded the solid ketodiacid which was heated neat to 200° C. and held at that temperature for 30 mins. to complete decarboxylation. Upon cooling, 1.14 g. of glassy 8a ketoacid was obtained (95%): mass spectrum m/e 400; UV (EtOH) 319, 273, 235, 205; IR (CHCl$_3$) cm$^{-1}$ 3500, 2500, 1710, 1655; NMR (CDCl$_3$) s 8.9 (br s, 1H), 7.62, 7.45 (both s, 1H), 6.65, 6.50 (≈4 lines, 2H), 6.02 (br s, 2H), 3.89 (s, 6H), 3.54 (s, 3H). This keto-acid consists of two diastereomers, as discussed in the next Example, but this mixture may be employed, without further processing, as the starting material of Example 9.

EXAMPLE 8

5,6,7,8-tetrahydro-7-carbomethoxy-2,3-methylenedioxy-10,11,12-trimethoxy-5-oxo-dibenzo[a,c]cyclooctadiene (8b)

Ketoacid 8a (100 mg, 0.25 mmol) was dissolved in 3% methanol-HCl (10 ml) and brought to reflux for 4 hrs. After cooling, the methanol was removed and the residue was dissolved in diethyl ether. The ether layer was washed successively with saturated sodium bicarbonate solution, saturated brine and dried over sodium sulfate. Filtration and evaporation of the solvent yielded the crude methyl ester 8b in good yield: IR (CHCl$_3$) cm$^{-1}$ 1728, 1653; NMR (CDCl$_3$), δ7.70, 7.51 (both s, 1H) 6.69, 6.63 (both s, 1H), 6.55, 6.50 (both s, 1H), 6.04 (br s, 2H), 3.90 (s, 6H), 3.73, 3.68 (both s, 3H), 3.58 (s, 3H), 3.2–2.3 (m, 5H). The ketoester 8b is a mixture of diastereomers which may be separated on silica gel TLC plates using 20% hexane in ether as chromatographic eluent. The less polar (more mobile) band gave a homogeneous diastereomer having aromatic proton singlets in the NMR (CDCl$_3$) at 67 7.70, 6.69 and 6.50. The more polar band gave a second diastereomer having aromatic proton singlets at δ7.51, 6.63 and 6.55. The former isomer corresponds to the "natural" atropisomeric configuration (ct stereoformula Va, p-10) and may be equilibrated (ca. 1=1) with the second isomer above 60°.

EXAMPLE 9

(±)-Steganone (IV)

Ketoacid 8a (180 mg, 0.45 mmol) was dissolved in 1N sodium hydroxide (0.5 ml) and 37% aqueous formaldehyde (44μL, 0.56 mmol) was added[13]. The reaction was placed under a nitrogen atmosphere and stirred at room temperature for 44 hrs. It was then acidified with excess 10% sulfuric acid. Chloroform (2 ml) was added and the mixture was heated just below reflux for 2 hrs. After cooling, the mixture was transferred to a separatory funnel and extracted into chloroform (25ml). The chloroform layer was separated, washed with saturated sodium bicarbonate solution (3 × 10 ml) which is saved to recover unreacted ketoacid, then with saturated brine (10 ml) and finally it was dried over sodium sulfate. Filtration and removal of the chloroform gave a residue which when triturated with methanol produced 75 mg of crystalline racemic steganone (40%), IV, m.p. 229°–230° C.: mass spectrum m/e 412, 308, 397, 328; U.V. (EtOH) 313, 274, 237; IR (CHCl$_3$) cm$^{-1}$ 1784, 1667; NMR (COCl$_3$) δ7.53 (s, 1H), 6.63 (s, 1H), 6.53 (s, 1H), 6.10 (s, 2H), 4.35 (m, 2H), 3.89 (s, 6H), 3.60 (s, 3H).

Anal. Calc'd. for C$_{22}$H$_{20}$O$_8$: C, 64.11; H, 4.85. Found: C, 64.30; H, 5.01.

[13]. D. Becker, L. R. Hughes, R. A. Raphael, *J. Chem. Soc., Chem. Commun.*, 431 (1974).
[14]. We thank Professor Kupchan for supplying authentic samples of steganacin and steganone. Chromatographic comparison of authentic and synthetic compounds were performed on silica gel using the following solvent systems: chloroform; benzene; 20% ethyl acetate, chloroform; 20% ethyl acetate, benzene, 20% ether, benzene; 40% acetone, hexane, 20% cyclohexane, ether; 50% cyclohexane, ether. HPLC comparison was made on 3 × 2 ft. × ¼ inch Corasil columns with chloroform as solvent at 0.6 ml/min.

EXAMPLE 10

(±)-Episteganol (V) and (±)-Steganol (III)

(±)-Steganone (310 mg., 0.75 mmol) was dissolved in methylene chloride (30 ml). Anhydrous methanol (30 ml) was added and the solution was cooled to 0°–5° C.

Sodium borohydride (300 mg., 79 mmol) was added with vigorous stirring. After 3 mins., the reaction mixture was poured into water (100 ml) and extracted into diethyl ether (2 × 100 ml). The ether layer was washed with water (3 × 50 ml), saturated brine (50 ml) and dried over sodium sulfate. Filtration and removal of solvents yielded about a 1:1 mixture of (±)-steganol and (±)-episteganol, which are separated by preparative layer chromatography on silica gel with 20% cyclohexane in diethyl ether as solvent; the episteganol moves faster in this system than steganol. (±)-steganol: m.p. 155°–158° C. (loss of methanol of crystallization); mass spectrum m/e 414, 396, 330; IR (CHCl$_3$) cm$^{-1}$ 3450, 1770; NMR (CDCl$_3$) s 6.78 (s, 1H), 6.57, (s, 1H), 6.45 (s, 1H), 6.02 (s, 2H), 3.89 (s, 3H), 3.85 (s, 3H), 3.73 (s, 3H).

(±)-episteganol: m.p. 215.5°–217.5° C; mass spectrum m/e 414, 396, 330; IR (CHCl$_3$) cm$^{-1}$ 3450, 1770, NMR (CDCl$_3$) δ7.08 (s, 1H), 6.69 (s, 1H), 6.50 (s, 1H), 6.03 (d, J=4, 2H), 4.96 (d, J=8, 1H), 3.89 (s, 6H), 3.59 (s, 3H).

EXAMPLE 11

(±)-Steganacin (I)

(±)-Steganol was heated to 50° C. in pyridine containing excess acetic anhydride under a nitrogen atmosphere for 6 hrs. Upon cooling, the reaction was poured into excess 10% sulfuric acid and the product was extracted into diethyl ether. The ether layer was washed with 10% sulfuric acid, water, saturated sodium bicarbonate solution, saturated brine, and then dried over sodium sulfate. Filtration and removal of the ether yielded a residue which crystallized on trituration with methanol to give crystalline (±)-steganacin, m.p. 212.5°–214.5° C., in near quantitative yield: mass spectrum m/e 456, 396, 366; IR (CHCl$_3$) cm$^{-1}$ 1770, 1730; NMR (CDCL$_3$) δ6.90 (s, 1H), 6.60 (s, 1H), 6.44 (s, 1H), 6.02 (s, 1H), 5.81 (d, J=7, 1H), 3.91 (s, 3H), 3.86 (s, 3H), 3.72 (s, 3H), 1.89 (s, 3H).

EXAMPLE 12

(±)-Steganangin (II)

Substitution in the procedure of example 11 for the acetic anhydride used therein of an equimolar quantity of angelic acid chloride produces the title compound II which is essentially identical in all respects with steganangin obtained from natural sources.

We claim:

1. A process for the preparation of a racemic mixture of the compound having the formula

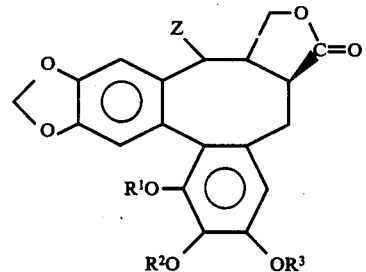

in which Z is ◀ OH, oxo (=O) or ◀ OW wherein W is acetyl or

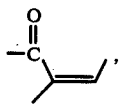

and $R^1$, $R^2$ and $R^3$ are alike or different and each is H or (lower)alkyl of 1 to 3 carbon atoms, which process comprises the consecutive steps of A. treating the compound having the formula

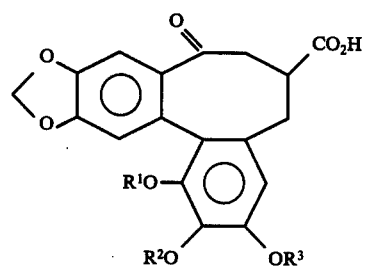

in which $R^1$, $R^2$ and $R^3$ are as defined above, with excess 37% aqueous formaldehdye in the presence of 0.1-2.0M alkali metal hydroxide for about 1 to 48 hours, followed by heating in the presence of excess dilute sulfuric acid and chloroform to produce the compound having the formula

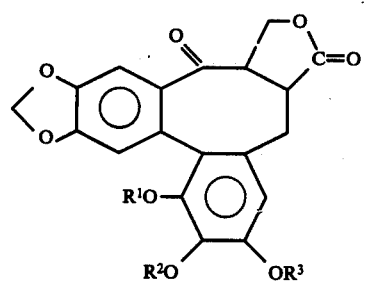         IV in which $R^1$, $R^2$ and $R^3$ are as defined above;

B. treating compound IV with sodium borohydride in methylene chloride-anhydrous methanol to produce a mixture of the compounds having the formula

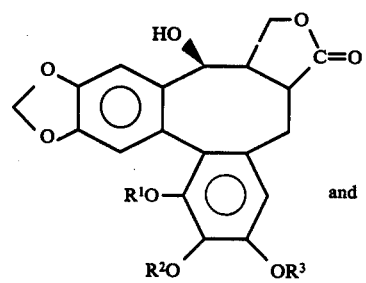         III and

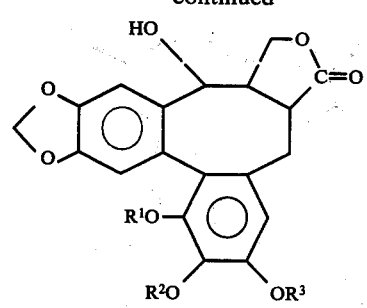         V in which $R^1$, $R^2$ and $R^3$ are as defined above, which mixture is separated into its component parts;

C. acylating compound III with acetic anhydride, acetyl halide or angelic acid halide in the presence of a tertiary amine to produce the compound having the formula

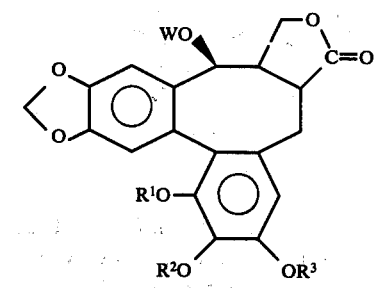

in which W is acetyl or

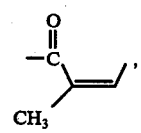

$R^1$, $R^2$ and $R^3$ are as defined above and halide is Cl, Br or I.

2. The process of claim 1 for the preparation of a racemic mixture of the compound having the formula

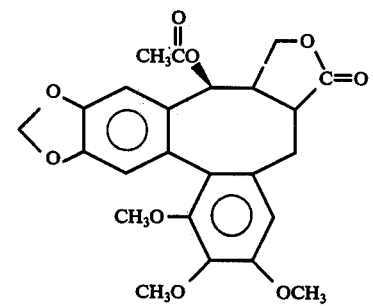         I which process comprises the consecutive steps of

A. treating the compound having the formula

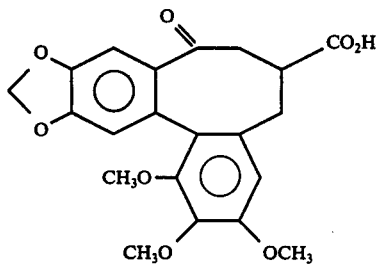

with a 25% molar excess of 37% aqueous formaldehyde in the presence of excess 1N sodium hydroxide at about room temperature for about 1 to 48 hours, followed by heating in the presence of excess 10% sulfuric acid and chloroform to produce the compound having the formula

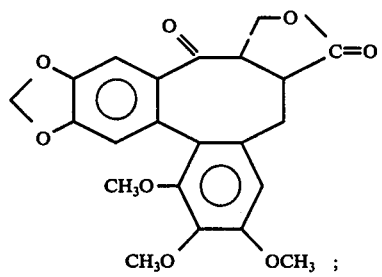

IV

B. treating compound IV with a slight molar excess of sodium borohydride in methylene chloride-anhydrous methanol for about 1 to 5 minutes, followed by quenching in water, to produce a mixture of the compounds having the formula

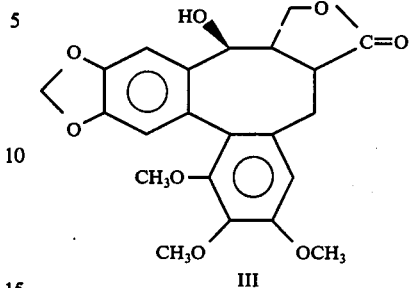

III and

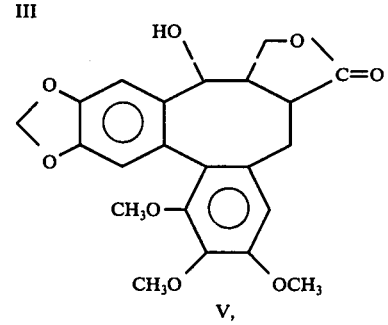

V, which mixture is separated into its component parts; and

C. acylating compound III with acetic anhydride or acetyl chloride in the presence of a tertiary amine selected from the group consisting of pryidine, trimethylamine, triethylamine, dimethylaniline and n-methylpiperidine with the aid of heat to produce compound I.

* * * * *

UNITED STATES PATENT AND TRADEMARK OFFICE
CERTIFICATE OF CORRECTION

PATENT NO. : 4,059,593

DATED : November 22, 1977

INVENTOR(S) : Andrew S. Kende and Lanny S. Liebeskind

It is certified that error appears in the above-identified patent and that said Letters Patent are hereby corrected as shown below:

In Column 2, at line 25, the structural formula should be

-- 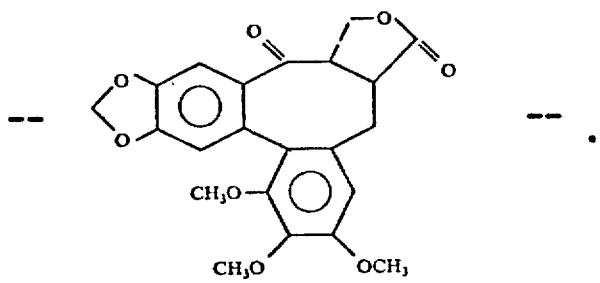 -- .

In Column 2, at line 40, the structural formula should be

-- 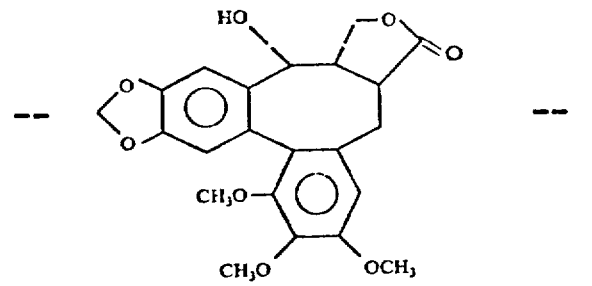 -- .

UNITED STATES PATENT AND TRADEMARK OFFICE
CERTIFICATE OF CORRECTION

PATENT NO. : 4,059,593
DATED : November 22, 1977
INVENTOR(S) : Andrew S. Kende and Lanny S. Liebeskind It is certified that error appears in the above–identified patent and that said Letters Patent are hereby corrected as shown below:

In Column 6, adjacent the reaction arrow in the middle of the page, insert --Example 10--.

In Column 8, at line 30, the structural formula should be

-- 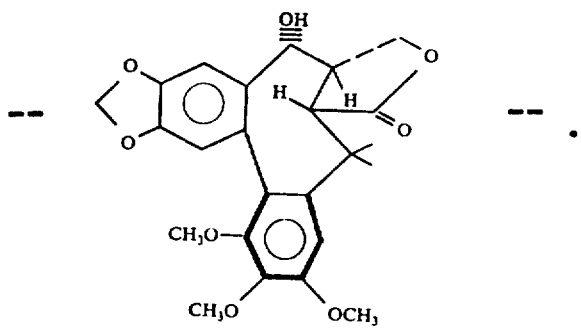 --.

In Column 8, at line 45, the structural formula should be

-- 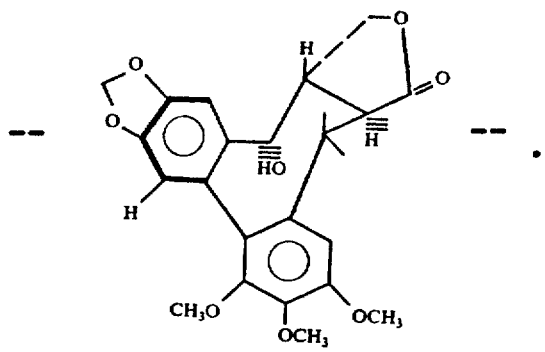 --.

UNITED STATES PATENT AND TRADEMARK OFFICE
CERTIFICATE OF CORRECTION

PATENT NO. : 4,059,593
DATED : November 22, 1977
INVENTOR(S) : Andrew S. Kende and Lanny S. Liebeskind It is certified that error appears in the above-identified patent and that said Letters Patent are hereby corrected as shown below:

In Column 12, line 2, "$CO_2R$ is H" should read --$CO_2R$, R is H--.

In Column 18, line 61, "8lower)alkyl" should read --(lower)alkyl--.

In Column 27, line 24, "67" should read --$\delta$--.

In Column 32, line 34, "n-methylpiperidine" should read --N-methylpiperidine--.

Signed and Sealed this

Seventh Day of March 1978

[SEAL]

Attest:

RUTH C. MASON
Attesting Officer

LUTRELLE F. PARKER
Acting Commissioner of Patents and Trademark